United States Patent [19]

Murray

[11] Patent Number: 4,483,334

[45] Date of Patent: Nov. 20, 1984

[54] EXTERNAL FIXATION DEVICE

[76] Inventor: William M. Murray, 145 Bryce Rd., Camp Hill, Pa. 17011

[21] Appl. No.: 483,622

[22] Filed: Apr. 11, 1983

[51] Int. Cl.³ .......................... A61F 5/04; B25G 3/36; E04G 7/00; F16B 00/00
[52] U.S. Cl. ................................. 128/92 A; 128/346; 403/391; 403/400
[58] Field of Search ................ 128/84 R, 84 B, 84 C, 128/92 R, 92 A, 92 E, 92 EA, 346; 403/385, 391, 400, 396

[56] References Cited

U.S. PATENT DOCUMENTS

| | | | |
|---|---|---|---|
| 2,250,417 | 12/1939 | Ettinger | 128/92 |
| 2,391,537 | 9/1943 | Anderson | 128/84 |
| 2,391,693 | 12/1943 | Ettinger | 128/84 |
| 2,406,987 | 1/1943 | Anderson | 128/85 |
| 2,439,995 | 4/1948 | Thrailkill | 128/92 A |
| 2,497,626 | 2/1950 | Persal | 128/92 A |
| 2,499,981 | 3/1950 | Strobel | 403/400 |
| 3,041,574 | 6/1962 | Cornell, Jr. | 403/396 |
| 3,096,110 | 7/1963 | Cantor | 403/385 |
| 3,951,372 | 4/1976 | Casler et al. | 403/385 |
| 3,961,854 | 6/1976 | Jaquet | 128/92 A |
| 4,258,708 | 3/1981 | Gentile | 128/92 |
| 4,273,116 | 6/1981 | Chiquet | 128/92 |

OTHER PUBLICATIONS

Hexcel Medical Products Advertisement, Nov. 1978.
Ace Orthopedic, Co. Advertisement, Nov. 1978.

Primary Examiner—C. Fred Rosenbaum
Assistant Examiner—C. W. Shedd
Attorney, Agent, or Firm—Thomas Hooker

[57] ABSTRACT

An external fixation device for holding bone segments in known relation to each other includes a pair of bone clamp assemblies each secured to bone pins extending from the bone segments, a bridge extending between the pin clamp assemblies and a specialized high friction universal assembly connecting the bridge to each of the pin clamp assemblies.

32 Claims, 10 Drawing Figures

EXTERNAL FIXATION DEVICE

The invention relates to a mechanical external fixation device for securing bone segments in known relation to each other during healing of fractures or other medical procedures. The external fixation device includes a pair of pin clamp assemblies for engaging pins extending from each bone segment, a bridge extending between the two pin clamp assemblies and a pair of specialized universal assemblies connecting the bridge to each pin clamp assembly.

Mechanical external fixation devices using pin clamp assemblies engaging bone pins extending from each of two bone segments and a bridge connecting the two pin clamp assemblies are shown in U.S. Pat. Nos. 2,250,417, 2,391,537, 2,406,987, 4,258,708 and 4,273,116. The commercially available Hexcel and Hoffman external fixation devices each include a bridge extending between two pin clamp assemblies. These devices are shown in advertisements in the Nov. 1978 issue of *Orthopaedic Review*.

The external fixation device of the present invention includes improved high friction universal assemblies connecting the bridge to the two pin clamp assemblies. Each universal assembly has a pair of pivoted hinge members with clamps which secure the hinge members to the bridge and one of the pin clamp assemblies. The pivot connection between the hinge members includes a plurality of intermeshing clamp leaves having circumferential clamp rings located outwardly of the pivot axis. Tightening of an operator forces the rings into frictional engagement to form a high torque connection which locks the hinge members together to form a rigid unit extending between the bridge and pin clamp assemblies. A single operator rigidly locks both of the clamps and the pivot connection between the hinge members.

The clamps securing the universal assemblies to the bridge and pin assemblies are provided with spacer and spring assemblies which bias the clamps toward the open position. In this way, loosening of the operators for both assemblies frees all of the connections formed by the universal assemblies to permit manual adjustment of the device during mounting on the bone pins. The loosened connections retain sufficient frictional drag so that the various components hold their positions until final alignment is achieved and the operators are tightened to form the desired rigid connections.

Each pin clamp assembly includes a pin tube and two tube clamps. The tube clamps carry pin clamps which engage bone pins. A single operator controls both the tube and pin clamps. The tube clamps are provided with spacer and spring assemblies which open the tube clamp as the operator is loosened while providing sufficient frictional drag on the tube clamp and pin clamp to enable manual rotation of the pin clamp on the tube clamp and rotation and shifting of the tube clamp on the pin tube. The surgeon may then manually locate these members in a desired orientation and have them retain this orientation until the operator is tightened forming a rigid connection between the bone pins and the pin tube.

The operators used to tighten the pin clamps and universal assemblies include threaded ends which engage threaded bores in these elements. The operator heads abut low area edges so that rotation of the various parts of the device as it is fitted to the bone pins does not clamp the elements together by tightening down the operator. Likewise rotation does not loosen the operators. Rather, the operators are rotated relative to the low area edges and are neither tightened nor loosened.

The elements of the external fixation bridge are preferably formed from stainless steel with the pin tubes formed from relatively thin walled stainless steel tubing. The bridge may be formed from stainless steel tubing or, alternatively, may include a stainless steel distractor or extender useful in biasing the bone segments toward or away from each other dependent upon the requirements of the particular application.

The device is of simple, lightweight construction and can be easily and quickly attached to bone pins extending from the bone segments. In comparison to conventional mechanical bridges, the bridge uses relatively few parts and is less expensive to manufacture. Its smooth and compact construction reduces snagging on surrounding objects, clothing and the like adjacent the patient, making the bridge much more comfortable during a recuperative period than conventional bridges.

Other objects and features of the invention will become apparent as the description proceeds, especially when taken in conjunction with the accompanying drawings illustrating the invention, of which there are four sheets and three embodiments.

In the Drawings:

FIGS. 8, 9 and 10 are perspective views of different embodiments of the external fixation device.

Figures 1, 2, 3:
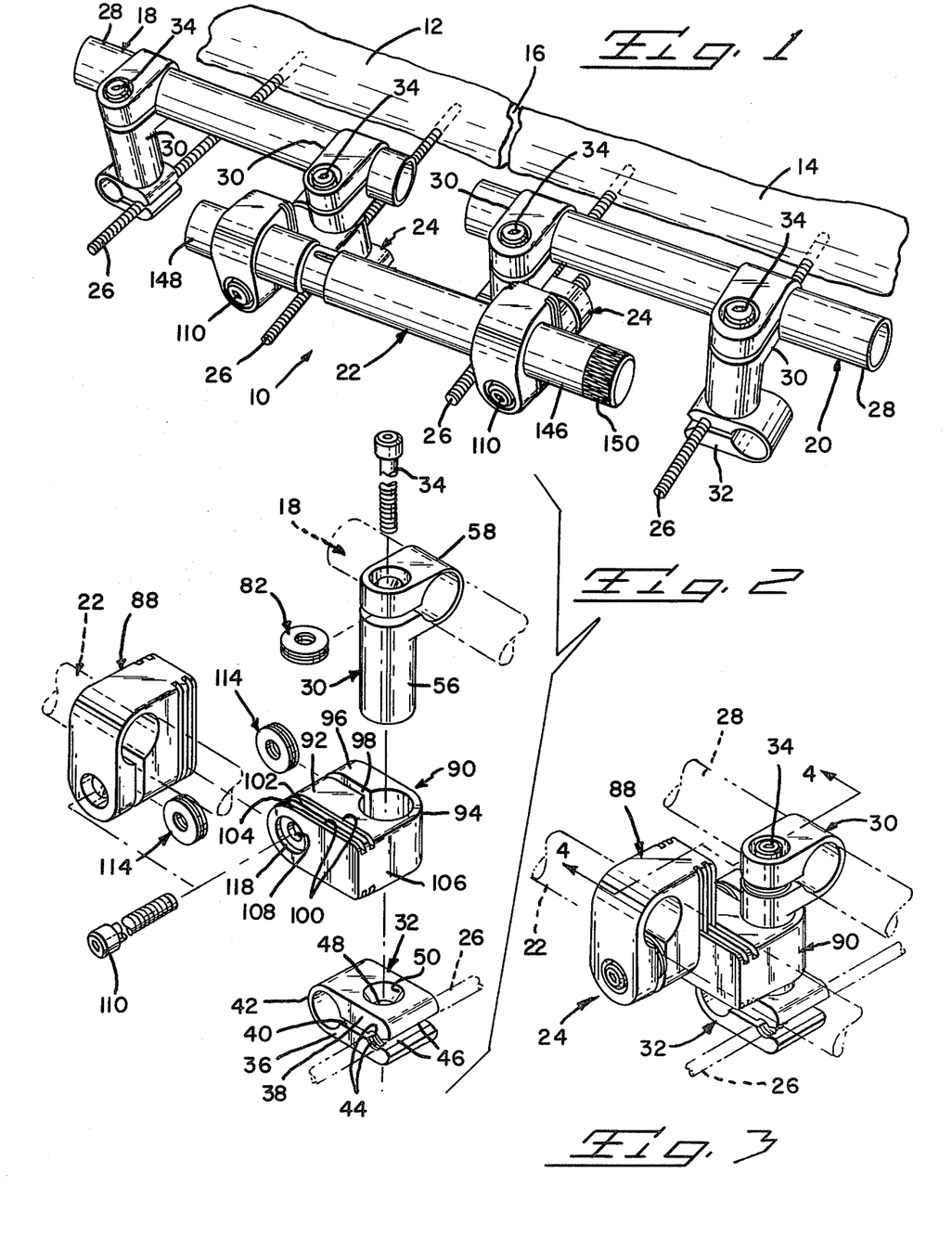
FIG. 1 is a perspective view of an external fixation device according to the invention.
FIG. 2 is an exploded view of a universal connection used in the device of FIG. 1.
FIG. 3 is enlarged perspective view of the universal connection.

External fixation device 10 shown in FIG. 1 is used to position two live bone segments 12 and 14 in fixed relationship to each other. In most applications, the device holds two fractured long bone segments together in axial alignment during healing of the fracture 16 between the segments. The device 10 may also be used to position bone segments during other procedures.

The device 10 includes a pair of like pin clamp assemblies 18 and 20 joined together by bridge 22. The bridge is connected to the pin clamp assemblies by a pair of like universal connections 24 shown more fully in FIGS. 2 through 6. Each pin clamp assembly 18, 20 is secured to a pair of conventional bone pins 26. The pins secured by clamp assembly 18 extend into bone segment 12 and the pins secured by clamp assembly 20 extend into bone segment 14.

Each pin clamp assembly 18, 20 includes a hollow pin tube 28, a pair of tube clamps 30 and a pair of pin clamps 32. Cap screws or operators 34 secure the pin clamps to the tube clamps and secure the tube clamps on the pin tubes 28. U-shaped pin clamps 32, as shown in FIG. 2 include legs 36 and 38 separated by a narrow slot 40 and connected together by a flexible integral hinge 42. Semi-cylindrical pin recesses 44 are provided in the adjacent faces of legs 36 and 38 a short distance inwardly of chamfered slot mouth 46. Each pin clamp 32 is mounted on a bone pin 26 as shown in FIG. 2 by positioning the mouth on one side of the pin and forcing the pin into the slot until it rests in the recesses 44. The bone pin 26 may be smooth or threaded. In the event a threaded pin is used, complimentary threads may be provided in recesses 44 to improve engagement between the clamp and pin.

Figures 4, 5:
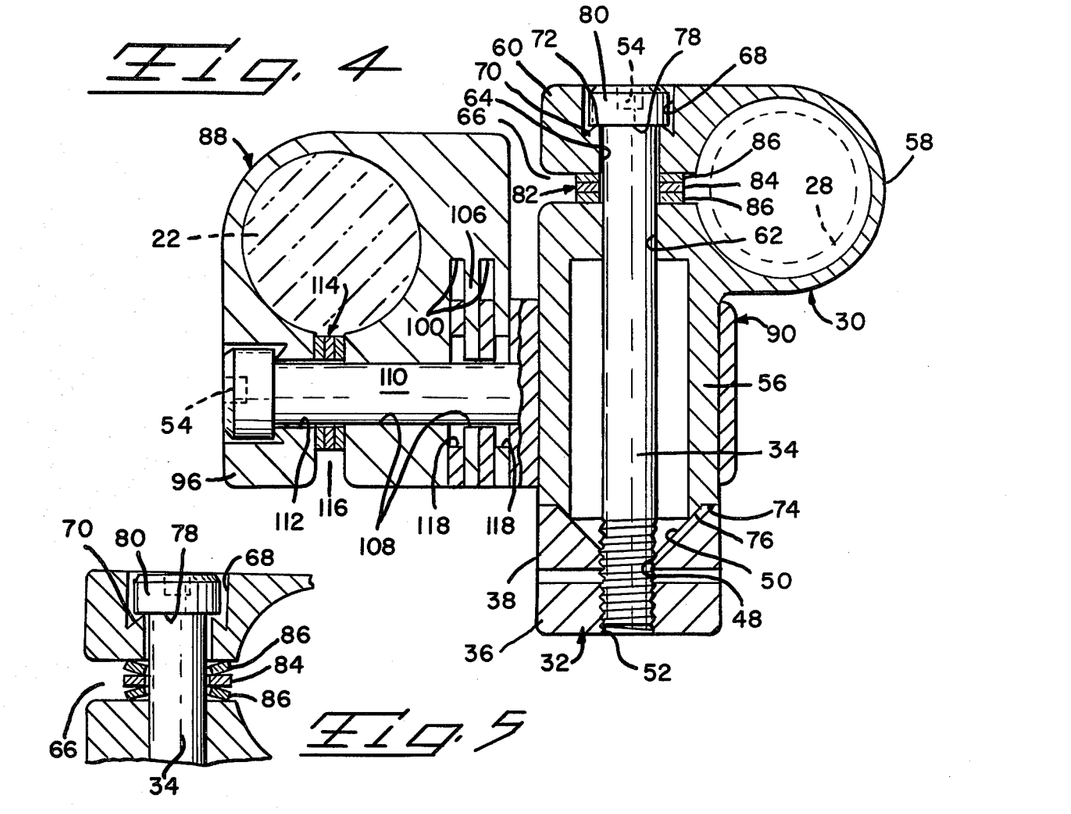
FIG. 4 is a sectional view taken along line 4—4 of FIG. 3.
FIG. 5 is a sectional view of a portion of a tube clamp of FIG. 4.
Figure 4:
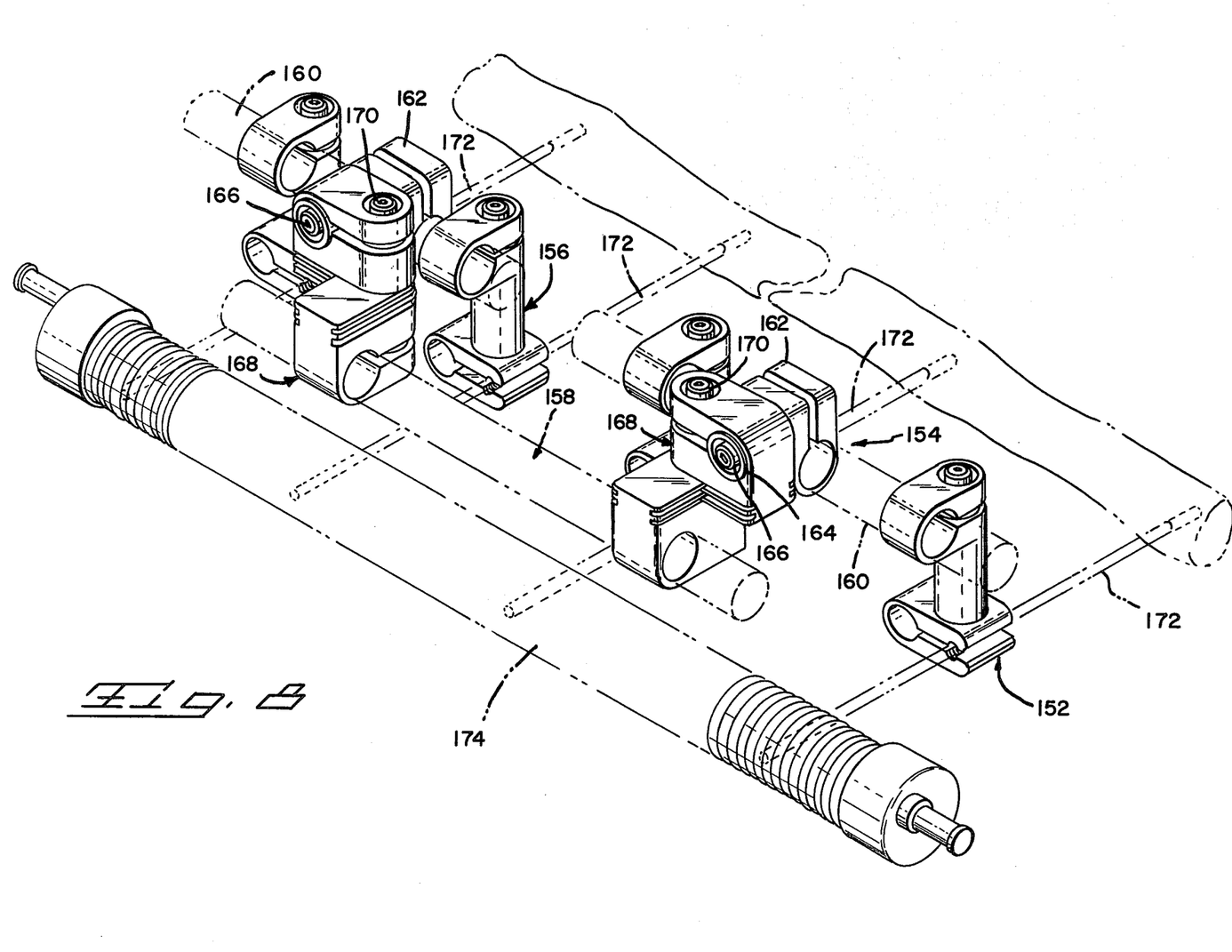

A bore 48 extends through both pin clamp legs 36 and 38 and is provided with a leveled-lead in 50 opening on the outer face of leg 38. The portion of the bore extending through leg 36 is provided with threads 52 for engagement with capscrew 34 as shown in FIG. 4. The threaded end of the capscrew extends freely through the bore in leg 38.

Tube clamps 30 include a hollow cylindrical stem 56 with a cylindrical band clamp 58 at one end and to one side of the stem as shown in FIGS. 2 and 4. Clamp leg 60 on the free end of the clamp 58 is positioned above the stem 56. An axial bore 62 extends through the stem and a slightly larger bore 64 extends through the clamp leg 60. The clamp leg and stem are separated by slot 66. Bore 64 opens into an enlarged cylindrical recess 68 on the side of leg 60 away from the stem 56. The reverse conical bottom wall 70 of bore 68 defines a low area circular edge 72 surrounding bore 64. The bottom of the stem 56 includes an outer cylindrical seating surface 74 surrounding an axially projecting conical locating ring 76.

The capscrew 34 extends through bores 64, 62 and 48 and engages threads 52 in the lower pin clamp leg 36. The flat bottom surface 78 of capscrew head 80 rests flush on edge 72. See FIG. 4. The pin clamp is positioned in proper alignment on the stem 56 by engagement of ring 76 in lead-in 50 on the pin clamp. Surface 74 rests flush on the top of the pin clamp leg 38.

Band clamp 58 extends around pin tube 28 and has a close sliding fit with the tube. A spacer and spring assembly 82 is provided in slot 66 in order to hold the band clamp open when the capscrew 34 is loosened and to provide a stop in the slot to prevent over tightening of the clamp and possible distortion of the pin tube. The assembly 82 includes a flat central washer 84 having a close sliding fit on the shaft of capscrew 34 and a pair of dished or Belleville washers 86 on the capscrew each to one side of flat washer 84. When the capscrew is tightened down to clamp the bone pin securely in place within pin clamp 32, secure the pin clamp in fixed relation on stem 56 and clamp the band 58 on the pin tube 28 the dished washers 86 are flattened as shown in FIG. 4 and serve to space clamp leg 60 from the the stem. In this position, the bore 64 is essentially coaxial with bore 62 and the tube clamp is rigidly secured to the pin tube.

The dished washers 86 are placed on capscrew 34 so that when they are relaxed or dish shaped the center hole of each washer is adjacent flat washer 84 while the outer circumference of each washer is adjacent the side walls of slot 66. When the capscrew is loosened the washers expand axially, thereby opening slot 66 and loosening the frictional engagement between band 58 and the pin tube and the frictional engagement between the stem and pin clamp. Expansion of the washers increases their inner diameters so that they become loose on the capscrew. The close sliding fit between washer 84 and the capscrew assures that the full spring amplitude of the washers is used to bias the clamp open.

For dished washers having the same inner and outer diameters, a thinner dished washer has a greater amplitude than a thicker dished washer. Assembly 82 uses a pair of relatively thin dished washers with a central flat washer having a thickness sufficient to assure that the thickness of the collapsed assembly provides proper clamping engagement between band 58 and the pin tube 28. When the capscrew is released, the dished washers 82 open the clamp 58 sufficiently for manual movement of the clamp on the tube. The capscrews 34 may be rotated from the fully clamped position to an adjustment position to provide a light, position retaining frictional loading between the clamp and pin tube and between the pin clamp 32 and stem 56. This loading allows a surgeon to position the pin and tube clamps manually as desired prior to tightening down the capscrews and forming permanent rigid connections.

When the tube clamp is open or closed, the assembly 82 expands and biases the edge 72 against surface 78, thereby assuring that the clamp leg follows the surface during opening and that the clamp is progressively opened or closed. The frictional engagement between low surface area of edge 72 and surface 78 is less than the high friction engagement between the threaded end of the capscrew and threads 52. This means that during initial set up of the tube clamp the surgeon may rotate the pin clamp with respect to the stem without tightening or loosening of the capscrew. Head 80 rotates on the low area edge 72. When the tube clamp is opened, clamp leg 60 pivots up from the position shown in FIG. 4 so that it is no longer coaxial with the capscrew. The oversize bore 64 prevents binding between the capscrew and clamp leg. FIG. 5 is illustrative and shows assembly 82 expanded further than required to adjust the pin and tube clamps.

Universal assembly 24, as shown in FIGS. 2, 3 and 4, includes a pair of similar hinge members 88 and 90. Each member includes a body 92 having a cylindrical band clamp 94 extending from one side of the body and ending at a free clamp leg 96 spaced from the other side of the body by a slot 98. A pair of narrow slots 100 extend from the other side of the body toward the first side at the end away from the band clamp 94 to define a pair of clamp leaves 102 and 104 having thicknesses the same as the width of the slots 100. The leaves are integrally joined to the body 92 at base 106 on the side of the body away from slot 98.

A bore 108 having a sliding fit with capscrew or operator 110 is formed through the thickness of body 92 and is coaxial with an enlarged bore 112 extending through clamp leg 96. An enlarged recess, reverse conical bottom and low area circular edge are provided at the end of the bore 112 at the outer surface of the leg 96. These features are similar to the recess, surface and edge 68, 70 and 72 of tube clamp 30. A spacer and spring assembly 114, like assembly 82, is provided in slot 116 between the body and the clamp leg 96, coaxial with bore 108. Bore 108 extends through the inner clamp leaf 102. An enlarged cylindrical bore 118, coaxial with bore 108, is formed through the outer leaf 104, as shown most clearly in FIG. 2.

Hinge member 90 is similar to the previously described hinge member 88 with the exception that the bore extending through the clamp leg 96 is threaded to engage the threaded end of capscrew 110. The bore 108 in hinge member 90 is slightly oversized to allow opening of the band clamp 94.

In the universal assemblies 24, hinge members 88 and 90 are pivoted together on capscrew 110 with the clamp leaves 102 and 104 of member 88 fitted within the slots 100 of member 90 as shown in FIG. 4. Capscrew 110 extends through the clamp leg 96 and body 92 of hinge member 88, the intermeshed clamp leaves, the body of member 90 and is threaded into the clamp leg of member 90.

In the external fixation device 10, the band clamp 94 of hinge member 88 extends around bridge 22 and the band clamp of hinge member 90 extends around the stem of an adjacent tube clamp 30. During initial adjustment of the universal assembly, the capscrew 110 is loosened to allow assemblies 114 to open the band clamps sufficiently so that they retain their positions on the stem and bridge but may also be manually adjusted by the surgeon as required by the particular application of the device. At the same time, the spring tension of assemblies 114 biases the intermeshed leaves 102 and 104 together so that the hinge members 88 and 90 may be manually pivoted with respect to each other about the cap groove 110 while there is sufficient friction between the leaves to maintain the members in a given position prior to tightening.

Tightening of the capscrew biases the clamp legs 96 toward each other to form a rigid high friction connection between the members and also between the individual members and the stem 56 and bridge 22. The large area friction connections formed by the band clamps 88 are similar to the connections formed by the band clamps 58 as previously described.

Tightening of capscrew 110 rigidly locks the hinge members together to prevent rotation about the axis of the capscrew. The intermeshed leaves 102 and 104 are positively clamped together between the bodies 92 of the two members outwardly of the circumference of the enlarged bores 118. Circumferential high friction connections are formed at the five meeting planes between the two members. These connections are located at a sufficient radius outwardly of the pivot axis of the two hinge members so that the additive frictional engagement rigidly locks the two members together against rotation. The connection is considerably stronger than the connection which would result without the enlarged bores 118 formed in leaves 104. The portions of the inner leaves 102 inside bores 118 are biased together when the capscrew is tightened but are not backed up against bowing apart and do not form an efficient frictional lock.

Figure 6:
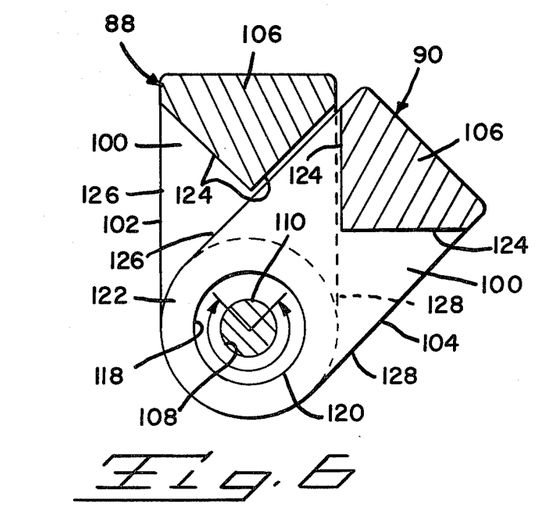
FIGS. 6 and 7 are sectional views taken through different types of pivot connections used in the universal connection.

FIG. 6 is a sectional view illustrating the hinge connection between members 88 and 90. The base 106 which connects the clamp leaves 102 and 104 to their respective bodies 92 has sides facing the capscrew 110 shaped to maximize the angle of rotation of one hinge member with respect to the other hinge member. In FIG. 6, hinge member 90 may be rotated about an angle 120 of about 270 degrees. The narrow slots 100 extend away from the capscrew pin 110 and beyond the enlarged bore 118 to provide desired circumferential high friction clamp areas 122 completely surrounding the screw. The base 106 is located outwardly of rings 122 and has two straight interior side edges 124. The side edges extend in from the base side of the member to an apex facing the rotational axis so that the slots 100 are concave adjacent the base. This concavity permits the intermeshed leaves to rotate close to the base, thereby increasing the maximum angle of rotation 120. In the case of the universal connection shown in FIG. 6, the top and bottom member walls 126 and 128 are parallel and the straight edges 124 intersect at an angle of 90°.

Figure 7:
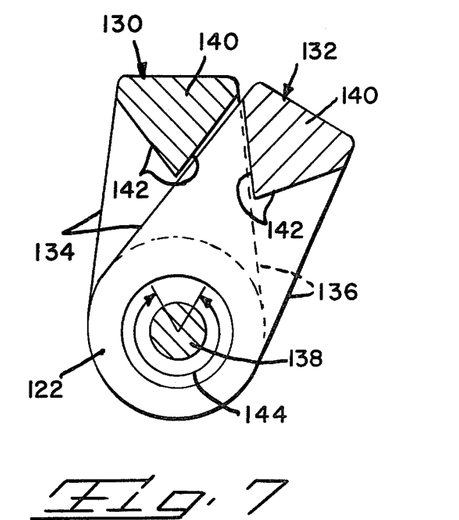

FIG. 7 is similar to FIG. 6 but illustrates a different type of universal assembly having hinge members 130 and 132 similiar to members 88 and 90 but with top and bottom walls 134 and 136 which decrease in thickness away from the capscrew 138 so that the thickness of bases 140 is reduced from that of the bases 106 shown in FIG. 6. The straight interior side edges 142 of bases 140 intersect at an angle less than 90 degrees so that member 142 may be rotated about an angle 144 of 300 degrees. The great rotational flexibility of the universal assemblies shown in FIGS. 6 and 7 permits the surgeon freedom of adjustment when orienting the bridge for a given procedure.

The bridge 22 is extendable and retractable and includes two coaxial cylindrical members 146 and 148 and an adjustment knob 150 on the free end of member 146. Rotation of knob 150 in one direction lengthens the bridge and rotation of the knob in an opposite direction contracts the bridge. Bridge 22 includes means to prevent relative rotation of members 146 and 148 so that the bridge, once properly adjusted, is equivalent to a rigid tube such as pin tubes 28. As shown in FIG. 3, universal assembly hinge members 88 are clamped to the bridge 22. Members 90 are clamped to stems 56. The bridge pin tubes and stems 56 are preferably of the same diameter.

The parts forming the external fixation device 10 are preferably formed from stainless steel. The pin tubes are preferrably rélatively thin walled stainless stell tubes. If desired, the adjustable bridge 22 may be replaced by a section of thin steel tubing similar to the tubing forming pin tubes 28.

The external fixation device 10 is readily attached to pairs of bone pins 26 extending from bone segments 12 and 14. Before attachment of the device on the pins, the capscrews or operators 34 and 110 are loosened to permit manual adjustment of the various members of the device. The surgeon clips the pin clamps 32 over the exposed ends of the bone pins so that the pins seat within recesses 44. Capscrews 34 are tightened, using an Allen wrench fitted into complimentary recesses 54 in the heads of the capscrews. Tightening of the capscrews 34 forms rigid connections between the pins tubes 28 and the bone pins 26. As shown in FIG. 1, the heads of screws 34 and 110 face upwardly and outwardly from the two assemblies and are readily accessible for adjustment and tightening.

Following positioning and tightening of the pin clamp assemblies 18 and 20, the surgeon manipulates these assemblies to locate the bone segments 12 and 14 in the desired clamped position. In the case of a fractured long bone, this position closes fracture 16. Capscrews 110 are loosened to permit manual rotation of the hinge members 90 about stems 56, hinge members 88 about and along the bridge 22 and the two members 88 and 90 with respect to each other about capscrews 110. The universal rotational freedom between the bridge and each pin clamp assembly and the freedom to move the universal assemblies on the bridge assembly permits the surgeon to orient and then secure the pin clamp assemblies in almost any desired permanent location.

In external fixation device 10, the hinge members 90 are clamped to the stems of the innermost tube clamps of the two assemblies 18, 20 and the hinge members 90 are located on the far sides of these tube clamps and are clamped to a relatively long bridge 22. This arrangement is convenient when used to orient broken long bones. The adjustability of the pin clamp and bridge assemblies permits the bridge to be attached to bone pins extending from bone segments in practically any given orientation.

FIG. 8 illustrates another embodiment of the invention where bridge 152 includes a pair of pin clamp assemblies 154 and 156 like previously described assemblies 18 and 20. These assemblies are joined by a bridge 158 which may be adjustable or one piece. The pin tube 160 of each clamp assembly 154, 156 carries an additional tube clamp 162 similar to tube clamp 30. Capscrews 166 extend through the stems of these tube clamps and are threaded to the remote legs of the tube clamps for locking the tube clamps on the tubes of their respective assemblies 145, 156. Universal assemblies 168, like the universal assembly 24 previously described, connect the bridge 158 to the clamp assemblies 154 and 156. The universal assemblies include band clamps surrounding the bridge and the stems of the tube clamps 162.

In FIG. 8, bone pins 172 are shown extending beyond the pin clamps of assemblies 154, 156 to permit an epoxy fixator 174 of the type descrived in Murray U.S. Pat. No. 3,877,424 to be skewered on the free ends of the pins following initial knitting of the bone fracture. After the fixator has set, the bridge 158 may be removed from the pins.

Figures 9, 10:
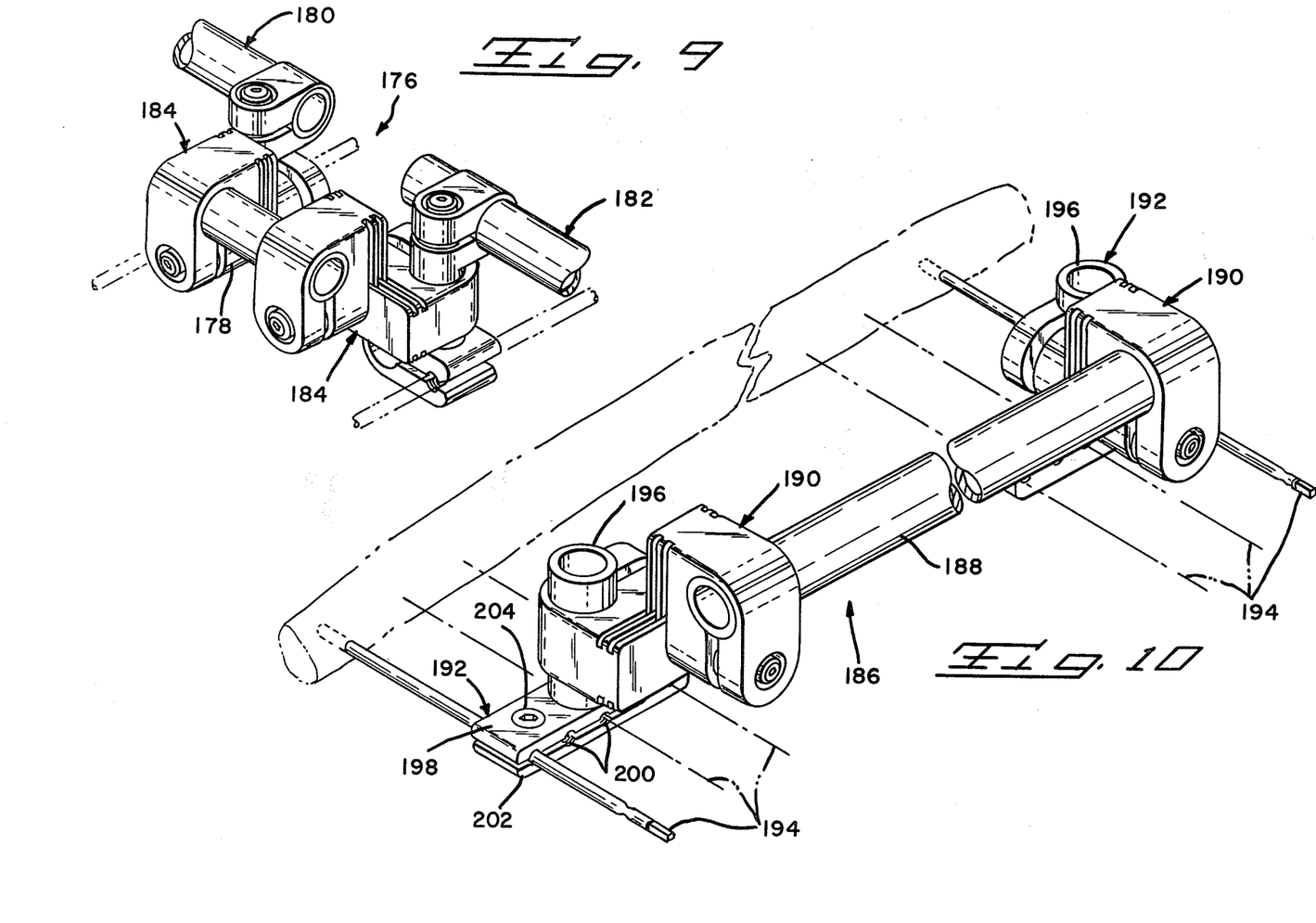

FIG. 9 illustrates an external fixation bridge 176 similiar to bridge 10 but with a very short and compact bridge 178. The bridge 178 is connected to pin clamp assemblies 180 and 182 like previously described pin clamp assemblies 18 and 20 by universal assemblies 184 like previously described universal assemblies 24 but with the hinge members surrounding the tube clamp stems extending into the space between the tube clamp assemblies. With this arrangement, the hinge members surrounding the bridge assembly tube are located close to each other thereby shortening the bridge and providing a particularly compact and light weight bridge.

External fixation bridge 186 shown in FIG. 10 includes a tubular bridge 188, a pair of universal assemblies 190 of the type previously described and a pair of pin clamp assemblies 192 particularly adapted to clamp onto spaced, parallel bone pins 194 extending from the bone segments held by the device. Each assembly 192 includes a stem 196 extending through the clamp of one of the universal assembly hinge members. The stem carries a pin clamp plate 198 having a number of spaced pin recesses 200 similar to previously described pin recesses 44. A clamp plate 202 is also provided with complimentary pin recesses 200 and is secured to plate 198 by suitable screws 204 (only one of which is illustrated). The pin clamp assemblies are rigidly secured to the bone pins by tightening screws 204 following which the pin clamp assemblies are rigidly joined by tightening the universal assemblies, as previously described.

The heads of the capscrews used in the disclosed bridges are recessed flush within their surrounding members and cannot snag on clothing or articles adjacent the bridge.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim my invention is:

1. An external fixation device for securing bone segments in known relation to each other comprising two pin clamp assemblies adapted to engage bone pins extending from bone segments, a bridge extending between the pin clamp assemblies and two adjustable assemblies each joining the bridge to a pin clamp assembly, at least one of the adjustable assemblies including a pair of members, a clamp on one member adjustably securing such member to the bridge and a clamp on the other member adjustably securing such member to one pin clamp assembly, each member including a clamp surface engagable with the clamp surface on the other member for locking the two members together, spring means biasing the clamps toward open positions and a common operator joining the members together with the clamp surfaces facing each other, said operator engaging said clamps such that acutation of the operator compresses the spring means, closes the clamps and forces said surfaces against each other to form a rigid connection between the bridge and the one pin clamp assembly.

2. An external fixation device as in claim 1 wherein each clamp includes a band and a clamp leg, and the operator comprises a screw having a head and a threaded end, the threaded end of the screw engaging the clamp leg of one clamp, the screw extending therefrom through passages in the members and past said surfaces and the screw head engaging a support surface on the clamp leg of said other clamp whereby rotation of the screw in one direction forces said legs toward each other to tighten the bands and bias said surfaces together to lock the members.

3. An external fixation device as in claim 2 wherein said spring means comprise springs located between the members and the clamp legs operable to bias the legs away from the members.

4. An external fixation device as in claim 3 wherein said springs surround the screw.

5. An external fixation device as in claim 4 including a spring assembly between each member and clamp leg including a spacer and a spring washer.

6. An external fixation device as in claim 5 wherein the spring assemblies each include a flat spacer washer having a close sliding fit on the screw and dished washers on the screw to either side of the flat washer with the small diameter bores of the dished washers biased toward the spacer washer, the thickness of the assemblies, when collapsed, determining the tightness of the clamps.

7. An external fixation device as in claim 2 wherein the head of said screw rests on a low area support whereby rotation of said members about the screw rotates the head relative to the clamp leg of said other clamp without rotating the threaded end of the screw relative to the clamp leg of said one clamp.

8. An external fixation device as in claim 7 wherein the head of the screw is seated within a recess within said other leg, the bottom of said recess defining a reverse surface having a low area edge engaging the screw head.

9. An external fixation device as in claim 2 wherein each member includes a plurality of clamp leaves having flat, parallel friction surfaces intermeshed with the clamp leaves of the other member, said screw extending through said leaves to lock said members together upon tightening of the screw.

10. An external fixation device as in claim 9 wherein the friction surfaces of each member are separated by slots and at least one leaf of each member includes a bore having a diameter greater than the diameter of the screw, such bore defining two engaged circumferential friction clamp surfaces spaced radially outwardly of the screw.

11. An external fixation device as in claim 10 wherein the slots extend a distance away from the clamp surfaces and are concave remote from the clamp surfaces to increase rotational adjustment of the members.

12. An external fixation device as in claim 10 wherein each member includes two clamp leaves, the large diameter bore being provided in the outermost leaf.

13. An external fixation device as in claim 2 wherein both adjustable assemblies are alike, the bridge is cylindrical, each pin clamp assembly includes a cylindrical member and each adjustable assembly is clamped to the bridge and to a cylindrical member.

14. An external fixation device for securing bone segments in known relation to each other comprising a pair of pin clamp assemblies; a bridge extending between the pin clamp assemblies; a pair of adjustable assemblies joining the bridge to the pin clamp assemblies; the pin clamp assemblies including a number of clamp members engaging bone pins extending from bone segments; at least one clamp member including a stem, a clamp on the stem engaging another part of the pin clamp assembly and having a clamp leg overlying one end of the stem, a bone pin clamp at the other end of the stem and an operator engaging the clamp leg and bone pin clamp whereby actuation of the operator tightens both the clamp and bone pin clamp to rigidly secure the bone pin to the pin clamp assembly, and spring means between the one end of the stem and the clamp leg biasing the clamp leg away from the stem and the bone pin clamp closed.

15. An external fixation device as in claim 14 wherein said operator comprises a screw having a head engaging the clamp leg and a threaded end engaging the bone pin clamp and the spring means surrounds the screw between the stem and clamp leg.

16. An external fixation device as in claim 15 including a spacer and spring assembly between the clamp leg and stem.

17. An external fixation device as in claim 16 wherein the spacer and spring assembly includes a flat spacer washer having a close sliding fit on the screw and dished washers on the screw to either side of the flat washer with the small diameter bores of the dished washer biased toward the spring washer, the thickness of the assembly, when collapsed, determining the tightness of the clamp.

18. An external fixation device as in claim 15 wherein the head of the screw rests on a low area support on the clamp leg whereby rotation of the bone pin clamp relative to the stem rotates the head relative to the clamp leg without rotating the threaded end of the screw in the bone pin clamp.

19. An external fixation device as in claim 18 wherein the head of the screw is seated within a recess in said free leg, the bottom of the recess defining a reverse surface having a low area edge engaging the screw head.

20. An external fixation device as in claim 15 wherein the stem is cylindrical and one of said adjustable assemblies is clamped to such surface.

21. An external fixation device as in claim 15 wherein all of said clamp members are alike, each pin clamp assembly including a cylindrical member and the clamp members surround such cylindrical members.

22. An external fixation device for securing bone segments in known relation to each other comprising two pin clamp assemblies adapted to engage bone pins extending from bone segments, a bridge extending between the pin clamp assemblies and two adjustable assemblies each joining the bridge to a pin clamp assembly, at least one of the adjustable assemblies including a pair of members, a clamp on one member adjustably securing such member to the bridge and a clamp on the other member adjustably securing such member to one pin clamp assembly, each member including at least one clamp leaf having flat, parallel friction surfaces and a common operator joining the members together with the leaves intermeshed and friction surfaces engaging each other, said operator engaging said clamps such that actuation of the operator closes the clamps and forces said friction surfaces against each other to form a rigid connection between the bridge and the one pin clamp assembly.

23. An external fixation device as in claim 22 wherein each clamp includes a band and a clamp leg, each member includes a plurality of leaves and the operator comprises a screw having a head and a threaded end, the threaded end of the screw engaging the free leg of one clamp, the screw extending through passages in the members and leaves and the screw head engaging a support surface on the clamp end of the other clamp whereby rotation of the screw in one direction forces said legs toward each other to tighten the bands and biases said leaves together to form a plurality of friction connections locking the members together.

24. An external fixation device as in claim 23 wherein the leaves of each member are separated by slots and at least one leaf of each member includes a bore having a diameter greater than the diameter of the screw, such bore defining two engaged circumferential clamp surfaces spaced radially outwardly of the screw.

25. An external fixation device as in claim 24 wherein the slots extend a distance away from the clamp surfaces and are concave remote from the clamp surfaces to increase rotational adjustment of the members.

26. An external fixation device as in claim 25 wherein the large diameter bores are in the outer most leaves of each member.

27. An external fixation device as in claim 23 including a spring means biasing both clamps open and the leaves toward each other.

28. An external fixation device as in claim 27 wherein each clamp includes a slot and the spring means comprises a spacer and two dished washers in each slot and on the screw, the spacer being located between the dished washers.

29. An external fixation device as in claim 23 wherein both adjustable assemblies are alike, the bridge is cylindrical, each pin clamp assembly includes a cylindrical member and each adjustable assembly is clamped to the bridge and to a cylindrical member.

30. An external fixation device for securing bone segments in a known relation to each other comprising two pin clamp assemblies adapted to engage bone pins extending from bone segments, a bridge extending between the pin clamp assemblies, two adjustable assemblies each joining the bridge to a pin clamp assembly, each adjustable assembly including a first adjustable clamp engageable with the bridge and a second adjustable clamp engagable with a pin clamp assembly, at least one clamp of one adjustable assembly including a band clamp having a free clamp leg separated from the remainder of the adjustable assembly by a slot, an operator engagable with said free leg to move the leg toward the remainder of the adjustable assembly so as to tighten the band clamp and a spring confined within said slot operable to bias said clamp open.

31. An external fixation device as in claim 30 including a spring assembly within the slot, said operator comprising a screw having a head engaging the clamp leg and extending through the spring assembly into the remainder of the adjustable assembly and having a threaded end engaging such remainder whereby tightening of the screw collapses the spacer and spring assembly.

32. An external fixation device as in claim 31 wherein the spring assembly includes a flat spacer washer having a close sliding fit on the screw and dished washers on the screw to either side of the flat washer with the small diameter bores of the dished washers biased toward the spacer washer, the thickness of the spacer and spring assembly, when collapsed, determining the tightness of the clamp.

* * * * *

UNITED STATES PATENT AND TRADEMARK OFFICE
CERTIFICATE OF CORRECTION

PATENT NO. : 4,483,334
DATED : November 20, 1984
INVENTOR(S) : William M. Murray It is certified that error appears in the above—identified patent and that said Letters Patent is hereby corrected as shown below:

In the Specification:

Column 1, line 18 change "Hoffman" to --Hoffmann--.

In the Claims:

Claim 23, line 5 change "free" to --clamp--.

Signed and Sealed this

Sixteenth Day of April 1985

[SEAL]

Attest:

DONALD J. QUIGG

Attesting Officer     Acting Commissioner of Patents and Trademarks